(12) United States Patent  
Roche et al.

(10) Patent No.: US 9,986,989 B2  
(45) Date of Patent: Jun. 5, 2018

(54) SURGICAL RETRACTOR FOR IMPLANTING LEADS AND METHODS OF MAKING AND USING

(71) Applicant: Boston Scientific Neuromodulation Corporation, Valencia, CA (US)

(72) Inventors: Julia A. Roche, Chula Vista, CA (US); Michael X. Govea, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days. days.

(21) Appl. No.: 15/397,693

(22) Filed: Jan. 3, 2017

(65) Prior Publication Data

US 2017/0196548 A1   Jul. 13, 2017

Related U.S. Application Data

(60) Provisional application No. 62/276,628, filed on Jan. 8, 2016.

(51) Int. Cl.
```
A61B 17/02    (2006.01)
A61B 1/06     (2006.01)
A61N 1/05     (2006.01)
A61N 1/372    (2006.01)
A61B 17/00    (2006.01)
```

(52) U.S. Cl.
CPC ............ *A61B 17/0218* (2013.01); *A61B 1/06* (2013.01); *A61B 17/0206* (2013.01); *A61B 17/0293* (2013.01); *A61N 1/05* (2013.01); *A61N 1/37205* (2013.01); *A61B 2017/00221* (2013.01); *A61B 2017/00407* (2013.01); *A61B 2017/00526* (2013.01)

(58) Field of Classification Search
CPC ............ A61B 17/0218; A61B 17/0206; A61B 17/0293; A61B 1/06; A61B 2017/00221; A61B 2017/00407; A61B 2017/00526; A61N 1/05; A61N 1/37205
USPC ....... 600/204, 208, 214, 219, 224, 226, 227, 600/233
See application file for complete search history.

(56) References Cited

U.S. PATENT DOCUMENTS 6,175,710 B1   1/2001   Kamaji et al.
6,181,969 B1   1/2001   Gord
(Continued)

OTHER PUBLICATIONS

U.S. Appl. No. 62/276,628, Entitled: Surgical Retractor for Implanting Leads and Methods of Making and Using, Inventor: Roche et al., filed Jan. 8, 2016, 35 pages.

*Primary Examiner* — Pedro Philogene
*Assistant Examiner* — David C Comstock
(74) *Attorney, Agent, or Firm* — Lowe Graham Jones PLLC; Bruce E. Black

(57) ABSTRACT

A retractor for implanting a lead of an electrical stimulation system includes multiple retractor teeth defining an implantation lumen; multiple pin arrangements that each include a base coupled to one of the retractor teeth and at least one pin extending from the base; a spiral track having multiple spiral indentations and multiple spiral ridges separating the spiral indentations with at least one pin of each of the pin arrangements engaging one of the spiral indentations of the spiral track; and a handle coupled to the spiral track to rotate the spiral track. The retractor is configured and arranged to radially move the retractor teeth as the spiral track is rotated.

20 Claims, 10 Drawing Sheets

(56) References Cited

U.S. PATENT DOCUMENTS

| | | |
|---|---|---|
| 6,224,450 B1 | 5/2001 | Norton |
| 6,271,094 B1 | 8/2001 | Boyd et al. |
| 6,295,944 B1 | 10/2001 | Lovett |
| 6,364,278 B1 | 4/2002 | Lin et al. |
| 6,391,985 B1 | 5/2002 | Goode et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,946,982 B2 | 5/2011 | Hamada |
| 7,949,395 B2 | 5/2011 | Kuzma |
| 7,974,706 B2 | 7/2011 | Moffitt et al. |
| 8,224,450 B2 | 7/2012 | Brase |
| 8,688,235 B1 | 4/2014 | Pianca et al. |
| 8,831,742 B2 | 9/2014 | Pianca et al. |
| 2005/0203347 A1* | 9/2005 | Fehling .............. A61B 1/31 600/210 |
| 2005/0215863 A1* | 9/2005 | Ravikumar ............ A61B 17/02 600/204 |
| 2006/0195017 A1 | 8/2006 | Shluzas et al. |
| 2007/0010716 A1* | 1/2007 | Malandain ............. A61B 90/35 600/224 |
| 2007/0150036 A1 | 6/2007 | Anderson |
| 2009/0187222 A1 | 7/2009 | Barker |
| 2009/0276021 A1 | 11/2009 | Meadows et al. |
| 2010/0076535 A1 | 3/2010 | Pianca et al. |
| 2010/0268298 A1 | 10/2010 | Moffitt et al. |
| 2011/0004267 A1 | 1/2011 | Meadows |
| 2011/0005069 A1 | 1/2011 | Pianca |
| 2011/0078900 A1 | 4/2011 | Pianca et al. |
| 2011/0130817 A1 | 6/2011 | Chen |
| 2011/0130818 A1 | 6/2011 | Chen |
| 2011/0238129 A1 | 9/2011 | Moffitt et al. |
| 2011/0301421 A1* | 12/2011 | Michaeli ............ A61B 17/0293 600/211 |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2013/0105071 A1 | 5/2013 | Digiore et al. |
| 2014/0114138 A1* | 4/2014 | Fedorov ............ A61B 17/0206 600/233 |
| 2015/0164496 A1* | 6/2015 | Karpowicz ........ A61B 17/0206 600/203 |

* cited by examiner

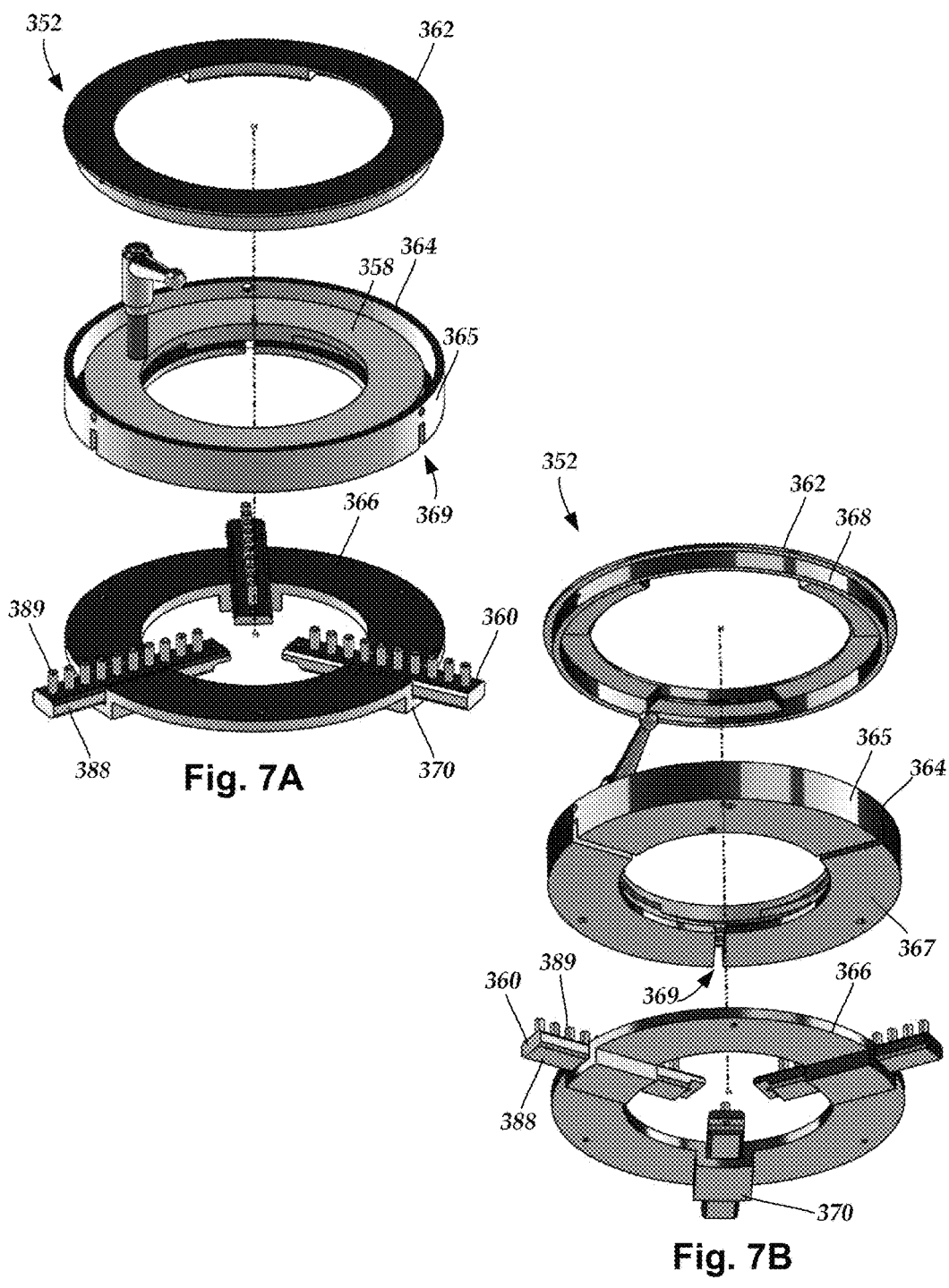

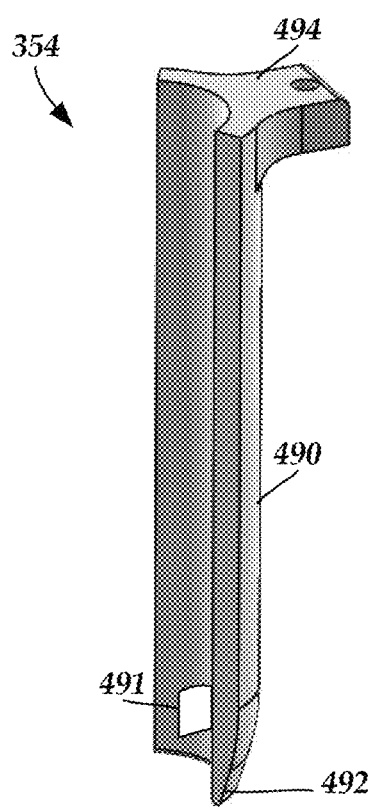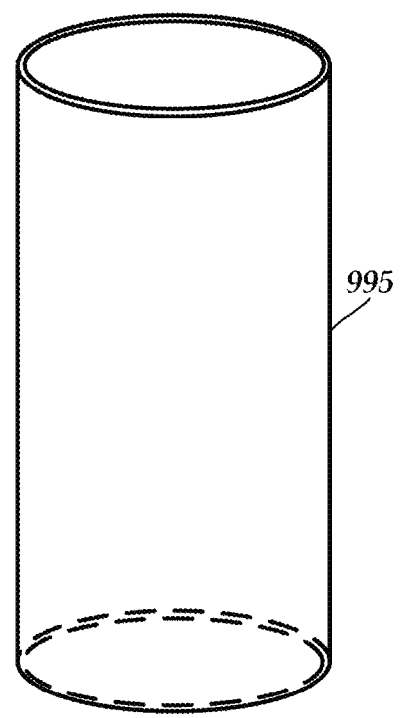
Fig. 9A
Fig. 9B

SURGICAL RETRACTOR FOR IMPLANTING LEADS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/276,628, filed Jan. 8, 2016, which is incorporated herein by reference.

FIELD

The present invention is directed to the area of implantable electrical stimulation systems and methods of making and using the systems. The present invention is also directed to surgical retractors for use in implanting leads of implantable electrical stimulation systems, as well as methods of making and using the retractors and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a retractor for implanting a lead of an electrical stimulation system. The retractor includes multiple retractor teeth defining an implantation lumen; multiple pin arrangements that each include a base coupled to one of the retractor teeth and at least one pin extending from the base; a spiral track having multiple spiral indentations and multiple spiral ridges separating the spiral indentations with at least one pin of each of the pin arrangements engaging one of the spiral indentations of the spiral track; and a handle coupled to the spiral track to rotate the spiral track. The retractor is configured and arranged to radially move the retractor teeth as the spiral track is rotated.

In at least some embodiments, each of the retractor teeth includes a distal end and each of the retractor teeth is tapered toward the distal end. In at least some embodiments, the number of pin arrangements is equal to the number of spiral indentations.

In at least some embodiments, the spiral track includes a gear arrangement formed on a surface of the spiral track opposite the spiral indentations. In at least some embodiments, the handle further includes a gear that engages the gear arrangement of the spiral track to couple the handle to the spiral track.

In at least some embodiments, the retractor further includes a hub arrangement, the hub arrangement including a hub housing that houses the spiral track, a lid disposed over the spiral track and engaged with the hub housing, and a bottom portion attached to the hub housing and engaging the pin arrangements. In at least some embodiments, the hub housing includes a base, a sidewall coupled to the base, and multiple slots where the pins of each of the pin arrangements are configured and arranged to slide along the slots. In at least some embodiments, the bottom portion includes multiple channels, where each of the pin arrangements is disposed in a different one of the channels and is configured and arranged to slide along the channel. In at least some embodiments, the lid includes a retraining ring configured and arranged to engage the spiral track.

In at least some embodiments, the retractor teeth and pin arrangements are formed of metal or rigid plastic. In at least some embodiments, the spiral track is formed of a plastic material having a lower coefficient of friction than the metal or rigid plastic.

In at least some embodiments, the retractor further includes a second handle coupled to the spiral track. In at least some embodiments, each of the retractor teeth includes a lighting element.

Another embodiment is an implantation kit that includes any of the retractors described above and an electrical stimulation lead having a distal portion and a proximal portion. The lead includes electrodes disposed along the distal portion of the lead, terminals disposed along the proximal portion of the lead, and conductors electrically coupling the terminals to the electrodes.

In at least some embodiments, the lead further includes a paddle body disposed along the distal portion of the lead, and at least one lead body extending from the paddle body, where the electrodes are disposed in at least two columns on the paddle body. In at least some embodiments, the implantation kit further includes a control module coupleable to the electrical stimulation lead. In at least some embodiments, the implantation kit further includes a series of dilators, where each dilator in the series has a diameter larger than a preceding one of the dilators in the series. In at least some embodiments, the implantation kit further includes an expandable sleeve to fit around the retractor teeth of the retractor.

Yet another embodiment is a method of implanting an electrical stimulation lead. The method includes providing any of the implantation kits described above; inserting the retractor teeth into tissue of the patient; rotating the spiral track to radially separate the retractor teeth; and implanting the electrical stimulation lead into the patient through the implantation lumen defined by the retractor teeth.

In at least some embodiments, the method further includes, after implanting, rotating the spiral track to bring the retractor teeth closer together; and removing the retractor teeth from the tissue of the patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7A is a schematic exploded top perspective view of one embodiment of a hub arrangement, spiral track, and pin arrangements of the retractor of FIG. 3, according to the invention;

FIG. 7B is a schematic exploded bottom perspective view of one embodiment of a hub arrangement, spiral track, and pin arrangements of the retractor of FIG. 3, according to the invention;

FIG. 9A is a schematic perspective view of another embodiment of a retractor tooth with a lighting unit, according to the invention;

FIG. 9B is a schematic perspective view of one embodiment of a sheath for use with the retractor of FIG. 3, according to the invention;

DETAILED DESCRIPTION

The present invention is directed to the area of implantable electrical stimulation systems and methods of making and using the systems. The present invention is also directed to surgical retractors for use in implanting leads, such as paddle leads, of implantable electrical stimulation systems, as well as methods of making and using the retractors and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 1:
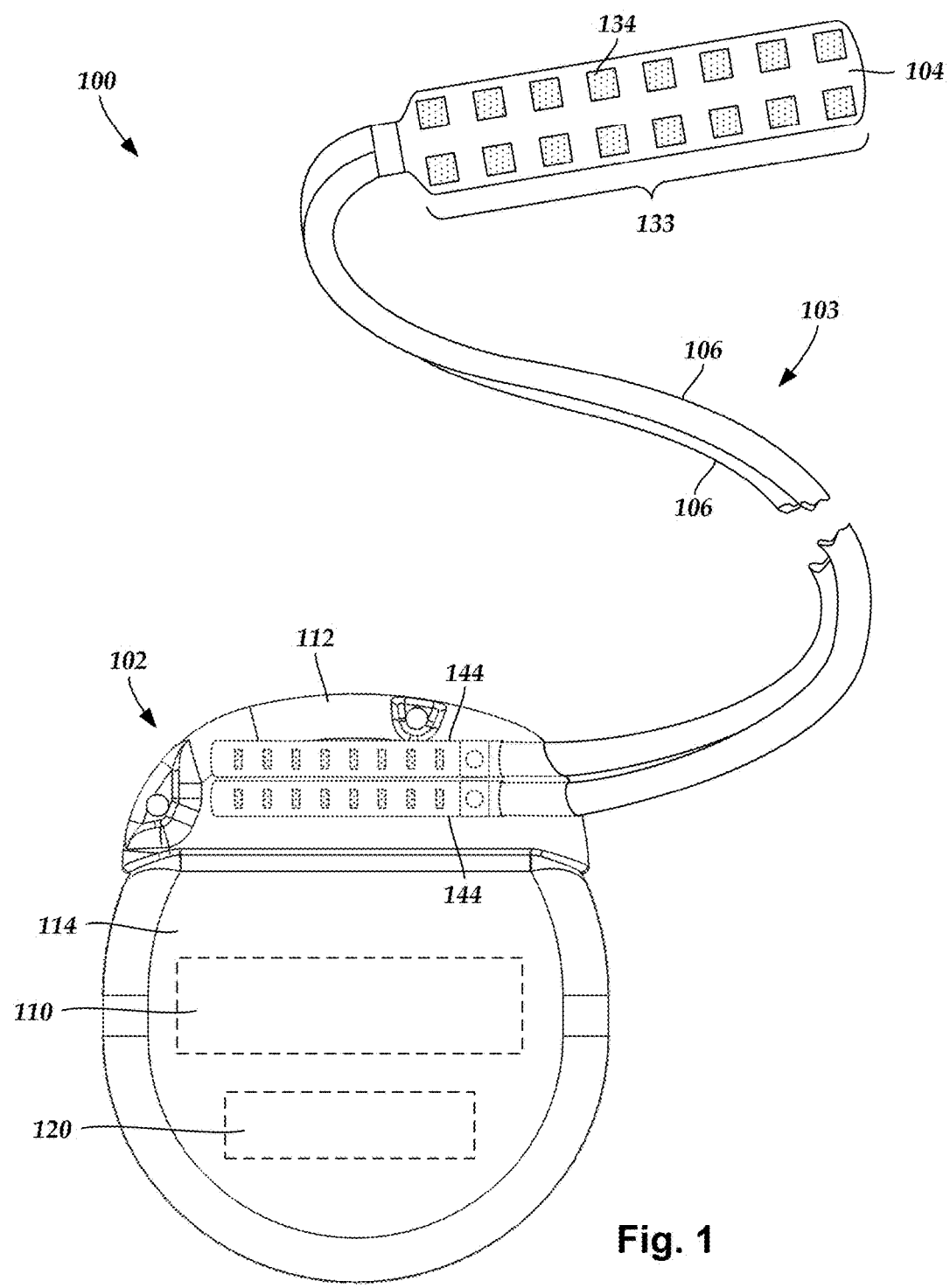
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 310 in FIG. 2A-2B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2A:
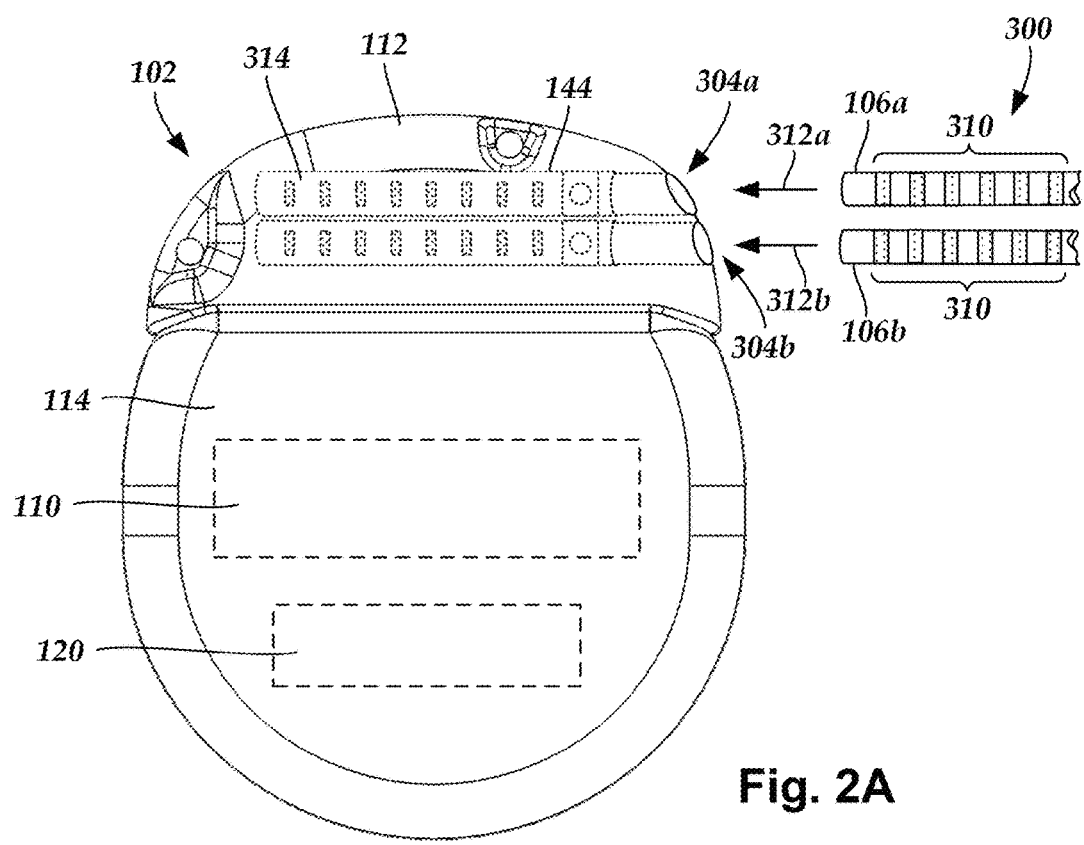
FIG. 2A is a schematic side view of one embodiment of the control module of FIG. 1 configured and arranged to electrically couple to an elongated device, according to the invention.
Figure 2B:
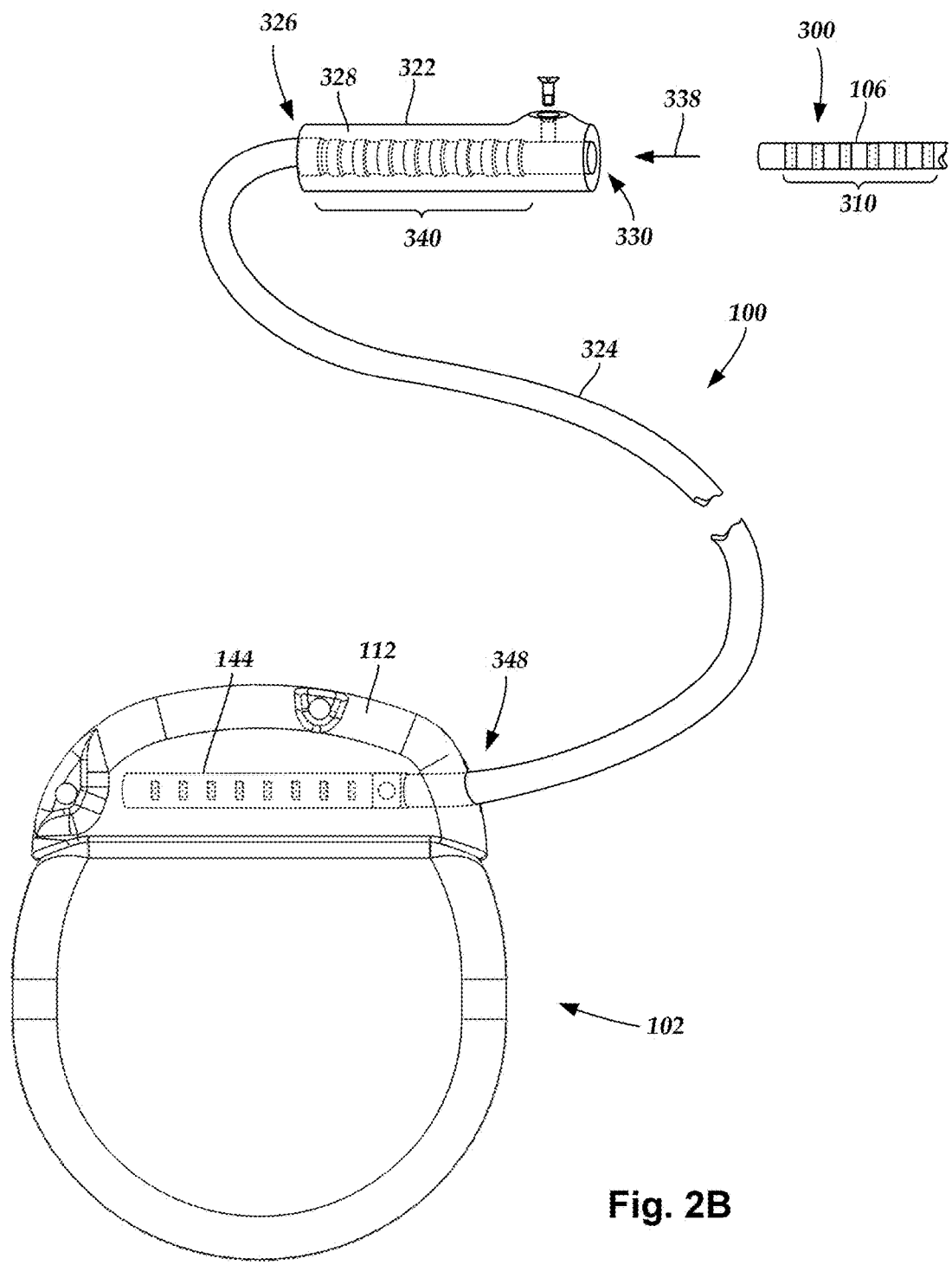
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204a and 204b of FIG. 1), or to receive multiple elongated devices 200 (e.g., both of the lead bodies 106 of FIG. 1), or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Paddle leads are often implanted into the spinal cord by laminectomy or laminotomy techniques. It is desirable, however, to identify other implantation methods that are less invasive. Such less invasive methods can have one or more advantages such as, for example, less patient or tissue trauma, a lower risk of infection, less healing time, less scarring, less surgical time, or any combination thereof. Tools can be developed to assist in percutaneous delivery and implantation of paddle leads.

Figure 3:
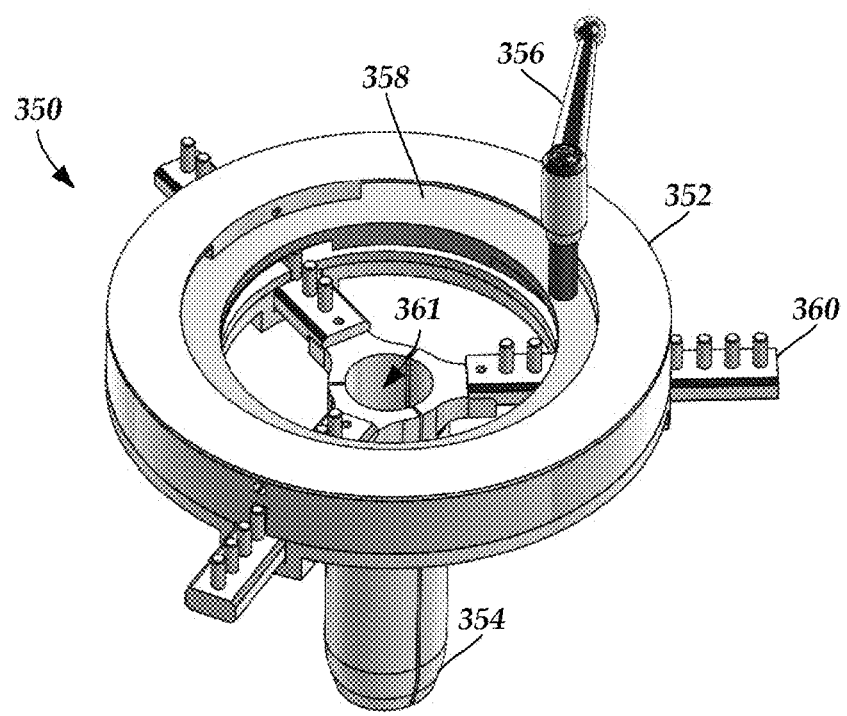
FIG. 3 is a schematic perspective view of one embodiment of a retractor, according to the invention.

As described herein, a retractor can be used for delivery and implantation of a paddle lead. FIG. 3 illustrates a retractor 350 having a hub arrangement 352, retractor teeth 354, a handle 356, and an implantation lumen 361 defined, at least in part, by the retractor teeth. The hub arrangement 352 includes a spiral track 358 and a pin arrangement 360 attached to each retractor tooth 354 to separate the retractor teeth as the handle is turned, as discussed in detail below. The retractor 350 can include any suitable number of teeth 354, such as, for example, two, three, four, five, six, or more teeth. In at least some embodiments, the retractor 350 will include an equal number of teeth 354 and pin arrangements 360 with each pin arrangement attached to a different one of the teeth.

Figure 4:
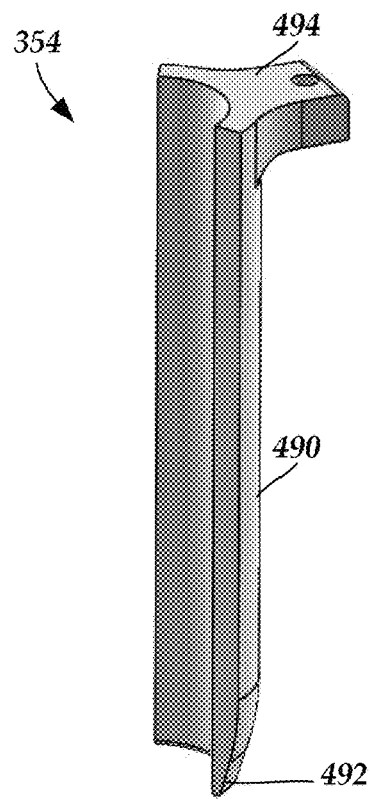
FIG. 4 is a schematic perspective view of one embodiment of a retractor tooth of the retractor of FIG. 3, according to the invention.

FIG. 4 illustrates one embodiment of a retractor tooth 354 which includes a shaft 490, a distal tip 492, and an attachment flange 494. The retractor teeth 354 can be formed of any suitable material including, but not limited to, metals or rigid plastics. The shaft 490 extends longitudinally and is intended to maintain an opening in the patient tissue to allow insertion of a lead (for example, a paddle lead) through an implantation lumen. In at least some embodiments, the lateral cross-sectional shape of the shaft 490 forms an arc. The distal tip 492 may be tapered, as illustrated in FIG. 4, to dilate tissue as the retractor teeth are inserted into the patient tissue. In some embodiments, the distal tip 492 may be sufficiently sharp to cut, or make incisions in, the tissue during insertion into the patient. The flange 494 is arranged for connection to one of the pin arrangements 360 or other component of the hub arrangement 352 so that the tooth 354 can moved through operation of the handle 356, as described in more detail below. In at least some embodiments, depending on the body type of the patient or the intended implant location (or both), the retractor teeth 354 can vary in length and size.

Figure 5A:
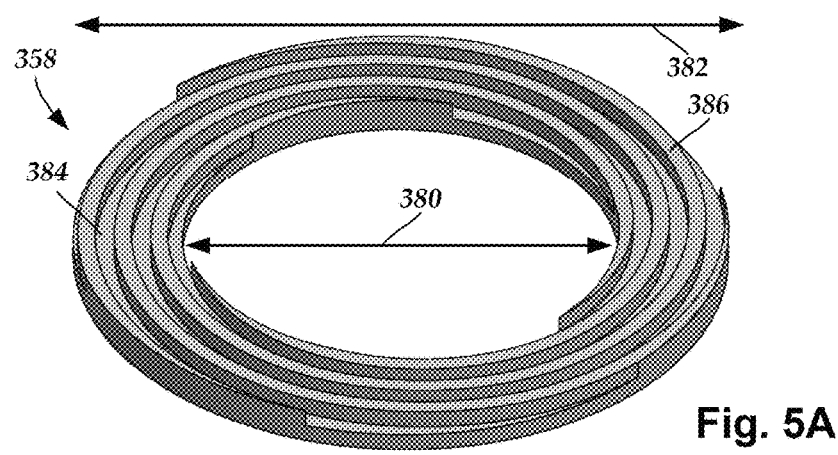
FIG. 5A is a schematic perspective view of one embodiment of a spiral track of the retractor of FIG. 3, according to the invention.

FIG. 5A illustrates one embodiment of the spiral track 358. The spiral track 358 has an inner diameter 380, an outer diameter 382, multiple spiral indentations 384, and multiple spiral ridges 386 separating the indentations. The inner diameter 380 can be selected to allow for access to the incision during the procedure. For example, the inner diameter can be 2, 3, 4, or more inches (approximately 2.5, 5.1, 7.6, 10.2, or more cm). The outer diameter 382 can be selected to permit sufficient separation of the retractor teeth 354 for implantation of the lead.

The spiral track 358 can have any number of spiral indentations 384 and spiral ridges 386. In at least some embodiments, the number of spiral indentations 384 is equal to, or more than, the number of retractor teeth 354. In at least some embodiments, the number of spiral ridges 386 is equal to, or one more or less than, the number of spiral indentations 384. In the illustrated example of FIG. 5A, the spiral track has three identical spiral indentations 384 and three identical spiral ridges 386 spaced circumferentially equidistant from each other.

Figure 5B:
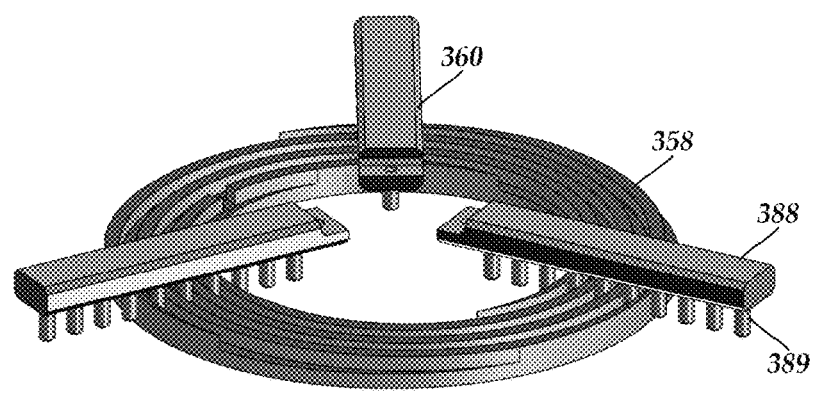
FIG. 5B is a schematic perspective view of one embodiment of a spiral track and pin arrangements of the retractor of FIG. 3 in a first position, according to the invention.
Figure 5C:
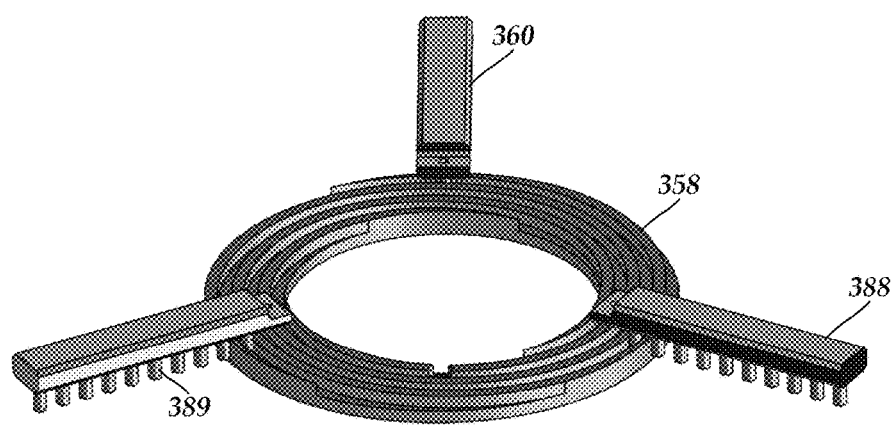
FIG. 5C is a schematic perspective view of one embodiment of a spiral track and pin arrangements of the retractor of FIG. 3 in a second position, according to the invention.
Figure 5D:
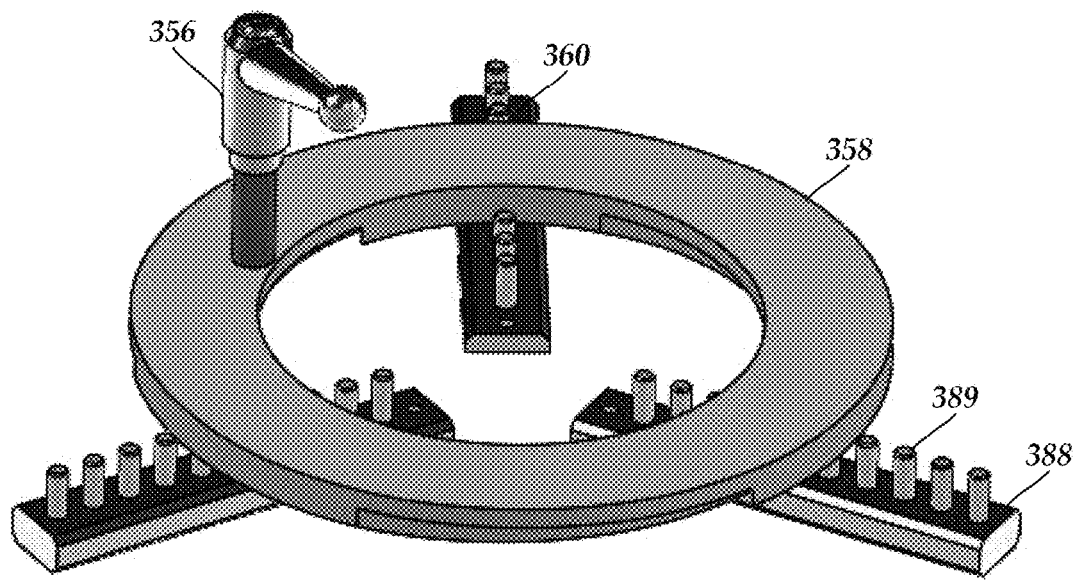
FIG. 5D is a schematic perspective view of one embodiment of a spiral track, handle, and pin arrangements of the retractor of FIG. 3 in the first position, according to the invention.
Figure 8A:
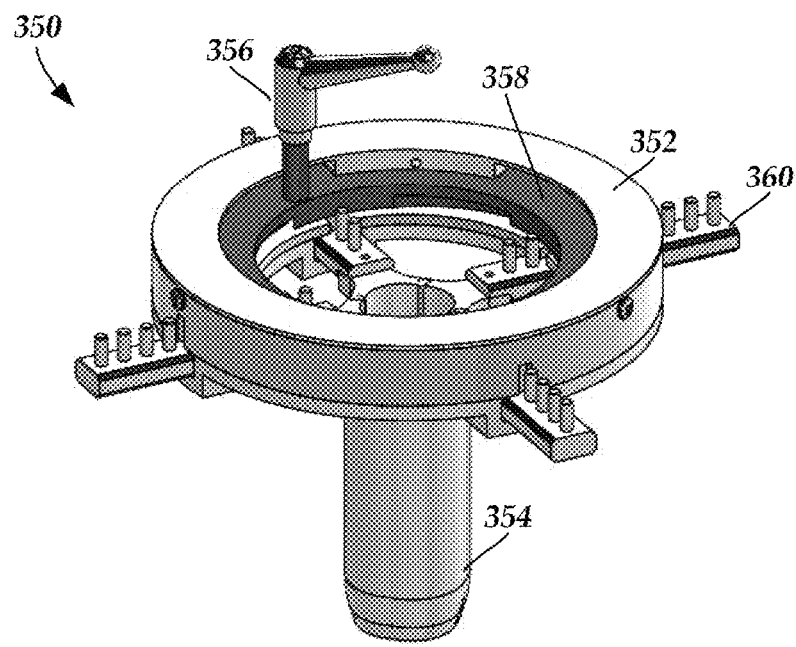
FIG. 8A is a schematic perspective view the retractor of FIG. 3 in a closed position, according to the invention.
Figure 8B:
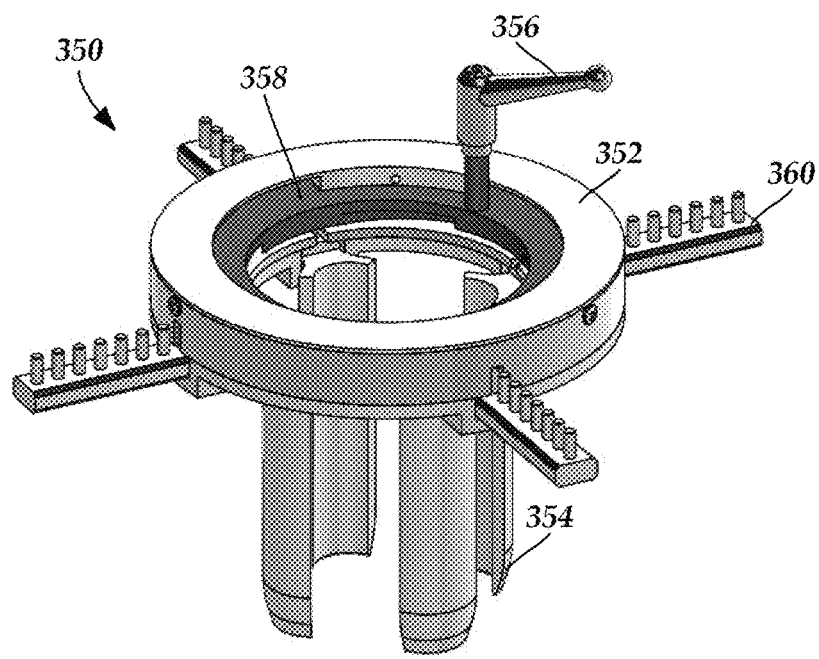
FIG. 8B is a schematic perspective view the retractor of FIG. 3 in one open position, according to the invention.

FIGS. 5B-5D illustrate the interaction between the spiral track 358 of FIG. 5A and one embodiment of the pin arrangements 360. Each pin arrangement 360 includes a base 388 and at least one pin 389 extending from the base. The pin arrangements 360 can be made from metal or hard plastic. Any number of pins can be used include one, two, three, four, five, six, seven, eight, or more pins. In at least some embodiments, each pin arrangement includes multiple pins. The spacing of the pins 389 is selected to fit within the spiral indentations 384 of the spiral track 358. As the spiral track 358 is rotated using the handle 356 (FIG. 5D), the pins 360 of the pin arrangements 360 slide along the spiral indentations 384 resulting in a radial movement of the pin arrangements 360 and the corresponding retractor teeth 354 (FIG. 3) attached to the pin arrangements, as illustrated by FIGS. 5B and 5C. Thus, the retractor teeth 354 can be separated when the handle 356 is moved in one direction (as shown in the sequence of FIGS. 8A and 8B) or brought together when the handle 356 is moved in an opposite direction. Optionally, one or more of the pin arrangements may include an end stop (not shown) that, when interacting with the spiral track 358, will halt further rotation of the spiral track and further separation of the retractor teeth 354. The spiral track can be made by, for example, molding or extrusion.

Figure 6:
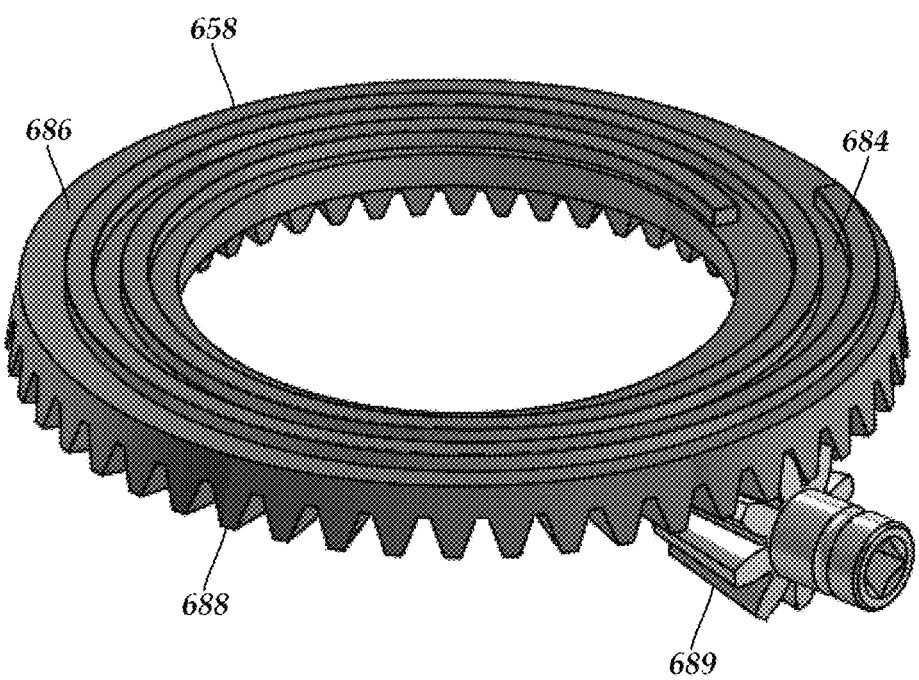
FIG. 6 is a schematic perspective view of another embodiment of a spiral track with a gear arrangement, according to the invention.

FIG. 6 illustrates another embodiment of a spiral track 658 with spiral indentations 684 and spiral ridges 686 on one side of the spiral track and a gear arrangement 688 on the opposite side of the spiral track. A gear 689 interacts with gear arrangement 688 to rotate the spiral track 658. A handle (not shown) is coupled to the gear 689. As the gear 689 is rotated, the gear arrangement 688 and spiral track 658 also rotate resulting in corresponding movement of the pin arrangement 360 (FIG. 5B) and retractor teeth 354 (FIG. 3). Depending on the gear ratio, additional mechanical advantage can be provided to the user.

FIGS. 7A and 7B are top and bottom exploded views of the hub arrangement 352 of the retractor 350 (FIG. 3). The hub arrangement 352 includes a lid 362, a hub housing 364, the spiral track 358, the handle 356, a bottom portion 366, and the pin arrangements 360. The lid 362 may be arranged to cover other components of the hub arrangement 352, such as the spiral track 358. The lid 362 may include a retaining ring 368 that fits over the spiral track 358 to facilitate maintaining the spiral track in the correct location while the spiral track is rotated.

The hub housing 364 includes a sidewall 365 and a base 367. The spiral track 358 fits within the sidewall 365 and on top of the base 367. The base 367 includes multiple slots 369 that receive the pins 389 of the pin arrangements 360 to prevent the pin arrangements from rotating with the spiral track 358 resulting, instead, in the radial motion of the pin arrangements when the spiral track 358 is rotated. In at least some embodiments, the number of slots 369 is equal to the number of pin arrangements 360.

The bottom portion 366 is coupled to the base 367 of the hub housing 364 and includes indented channels 370 for receiving the base 388 of the pins arrangements 360 and to allow the pin arrangements to slide radially along the indentations 370.

In at least some embodiments, the retractor 350 is primarily made out of metal or hard plastic. Optionally, the spiral track 358 can be made a low friction material, such as polytetrafluoroethylene (PTFE), such that the spiral track has a lower index of friction than the metal or hard plastic of other components of the retractor 350. In some embodiments, the pins may also be made of the same or different low friction material. The components can be machined, molded, or made via additive manufacturing, or any combination thereof.

As one example of the use of the retractor 350, an incision (for example, about 2 inches (or 5 cm) long) is made at the area of interest on the patient back. Then, a series of tubular dilators (not shown, but the same as, or similar to, the series of hollow introducers described in U.S. Pat. No. 8,849,422, incorporated herein by reference) are used to dilate the incision to the same diameter as the retractor 350. The retractor 350 in the closed position (FIG. 8A) is inserted over the final dilator until the retractor teeth are sufficiently deep to perform a laminotomy. The final dilator is then removed. The spiral track 358 of the retractor 350 is rotated which forces the retractor teeth 354 to move outward in a radial direction to a retracted position (FIG. 8B), thus retracting the soft tissue and muscle at the incision site.

Once the desired dilation of the incision has been achieved, the spiral track 358 is preferably not rotated further. In at least some embodiments, the retractor 350 will remain locked in place after it has been dilated due to the arrangement of the components of the retractor. The practitioner can then perform the laminotomy and paddle lead (or other lead) implant procedure. After the lead has successfully been placed, the spiral track 358 of the retractor 350 can then be spun back to its closed position (FIG. 8A) and the retractor can be removed from the patient.

A variety of optional attachments can be used in conjunction with the retractor 350. For example, lighting, such as LED lighting, can be inserted through the retractor. Alternatively or additionally, lighting units 491 (such as LED lighting units) can be provided on the interior on the retractor teeth 354, as illustrated in FIG. 9A, to provide more lighting during the implant procedure.

Another optional attachment is an expandable sleeve 495 (for example, a silicone sleeve), illustrated in FIG. 9B, is disposed on the exterior of the retractor teeth 354 to prevent soft tissue from entering the surgical field and interfering with the procedure. The sleeve can expand as the retractor teeth separate (FIG. 8B).

Optionally, one or more additional handles can be coupled to the spiral track to provide better leverage for the user. In addition, clearing tools, such as a bone removal tool or tissue removal too or dilator, can be included for insertion through the retractor 350 to assist in gaining access to the desired surgical area.

Figure 10:
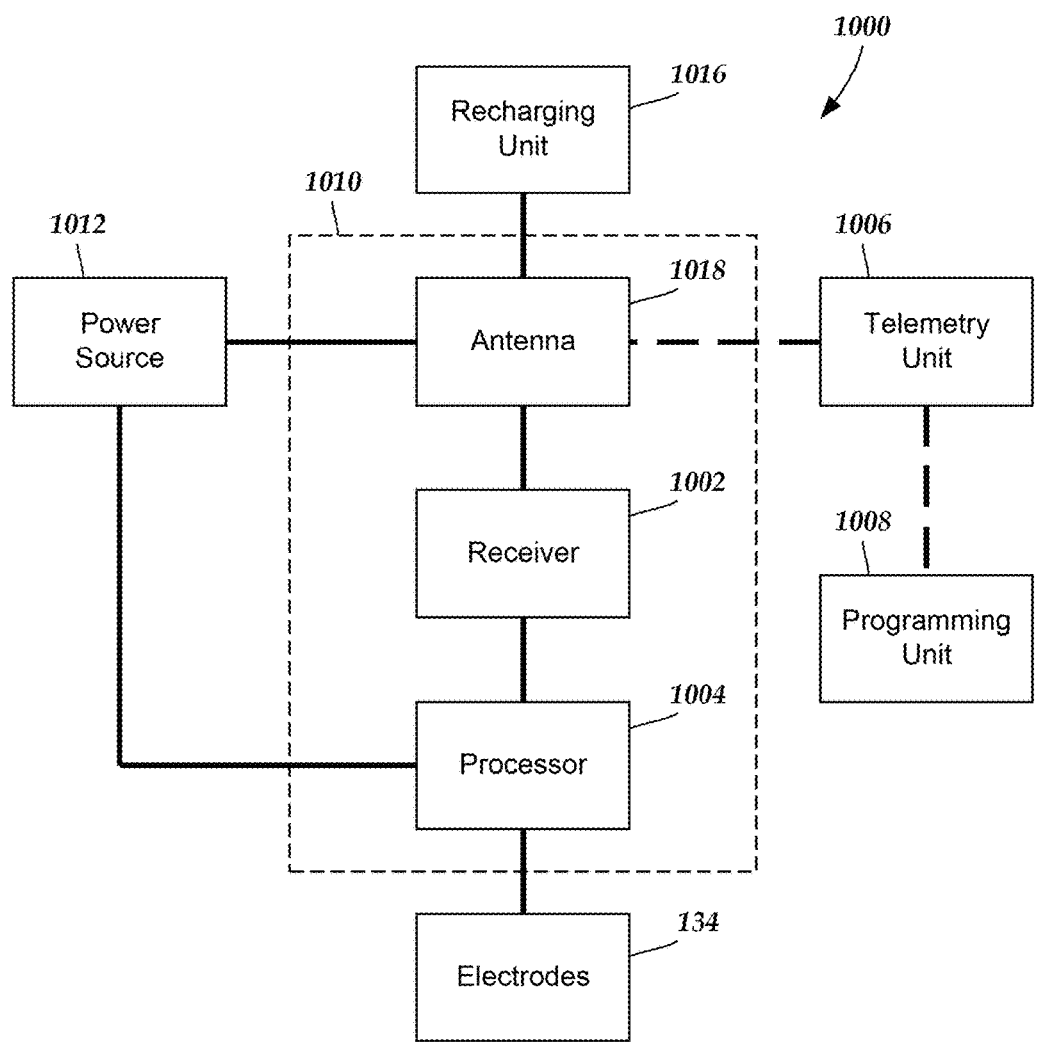
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, a power source 1012, an antenna 1018, a receiver 1002, and a processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 selects which electrode(s) are cathodes and which electrode(s) are anodes. In some embodiments, the processor 1004 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by the programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection.

One example of a suitable programming unit is a computer operated by the user or clinician to send signals to the telemetry unit 1006.

The signals sent to the processor 1004 via the antenna 1018 and the receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include the antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A retractor for implanting a lead of an electrical stimulation system, the retractor comprising:
    a plurality of retractor teeth defining an implantation lumen;
    a plurality of pin arrangements, each pin arrangement comprising a base coupled to one of the retractor teeth and a plurality of pins extending from the base;
    a spiral track comprising a plurality of spiral indentations and a plurality of spiral ridges separating the spiral indentations, wherein at least one of the pins of each of the pin arrangements engages one of the spiral indentations of the spiral track and the pins of each pin arrangement are spaced apart to permit simultaneous engagement of two of the pins of the pin arrangement with two different ones of the spiral indentations; and
    a handle coupled to the spiral track and configured and arranged to rotate the spiral track, wherein the retractor is configured and arranged to radially move the retractor teeth as the spiral track is rotated.

2. The retractor of claim 1, wherein each of the retractor teeth comprises a distal end, wherein each of the retractor teeth is tapered toward the distal end.

3. The retractor of claim 1, wherein a number of the pin arrangements is equal to a number of the spiral indentations and each of the spiral indentations extends at least 360 degrees around the spiral track.

4. The retractor of claim 1, wherein the spiral track comprises a gear arrangement formed on a surface of the spiral track opposite the spiral indentations.

5. The retractor of claim 4, wherein the handle further comprises a gear that engages the gear arrangement of the spiral track to couple the handle to the spiral track.

6. The retractor of claim 1, wherein the retractor further comprises a hub arrangement, the hub arrangement comprising a hub housing that houses the spiral track, a lid disposed over the spiral track and engaged with the hub housing, and a bottom portion attached to the hub housing and engaging the pin arrangements.

7. The retractor of claim 6, wherein the hub housing comprises a base, a sidewall coupled to the base, and a plurality of slots, wherein the pins of each of the pin arrangements are configured and arranged to slide along the slots.

8. The retractor of claim 6, wherein the bottom portion comprises a plurality of channels, wherein each of the pin arrangements is disposed in a different one of the channels and is configured and arranged to slide along the channel.

9. The retractor of claim 1, wherein the retractor teeth and pin arrangements are formed of metal or rigid plastic.

10. The retractor of claim 9, wherein the spiral track is formed of a plastic material having a lower coefficient of friction than the metal or rigid plastic.

11. The retractor of claim 1, further comprising a second handle coupled to the spiral track.

12. The retractor of claim 1, wherein each of the retractor teeth comprises a lighting element.

13. An implantation kit, comprising:
    the retractor of claim 1; and
    an electrical stimulation lead having a distal portion and a proximal portion, the lead comprising:
        a plurality of electrodes disposed along the distal portion of the lead,
        a plurality of terminals disposed along the proximal portion of the lead, and
        a plurality of conductors electrically coupling the terminals to the electrodes.

14. The implantation kit of claim 13, wherein the lead further comprises
    a paddle body disposed along the distal portion of the lead, and
    at least one lead body extending from the paddle body,
    wherein the electrodes are disposed in at least two columns on the paddle body.

15. The implantation kit of claim 13, further comprising a control module coupleable to the electrical stimulation lead.

16. The implantation kit of claim 13, further comprising a series of dilators, wherein each dilator in the series has a diameter larger than a preceding one of the dilators in the series.

17. The implantation kit of claim 13, further comprising an expandable sleeve configured and arranged to fit around the retractor teeth of the retractor.

18. A method of implanting an electrical stimulation lead, the method comprising:
    providing the implantation kit of claim 13;
    inserting the retractor teeth into tissue of the patient;
    rotating the spiral track to radially separate the retractor teeth; and
    implanting the electrical stimulation lead into the patient through the implantation lumen defined by the retractor teeth.

19. The method of claim 18, further comprising
    after implanting, rotating the spiral track to bring the retractor teeth closer together; and
    removing the retractor teeth from the tissue of the patient.

20. The retractor of claim 1, wherein the handle, pin arrangements, and spiral track are configured and arranged to rotate the spiral track at least 360 degrees.

\* \* \* \* \*